United States Patent [19]
Zolner

[11] 3,963,928
[45] *June 15, 1976

[54] MULTIPLE CHAMBER CHEMILUMINESCENT ANALYZER

[75] Inventor: William J. Zolner, Westford, Mass.

[73] Assignee: Thermo Electron Corporation, Waltham, Mass.

[ * ] Notice: The portion of the term of this patent subsequent to May 6, 1992, has been disclaimed.

[22] Filed: Mar. 17, 1975

[21] Appl. No.: 558,749

Related U.S. Application Data

[63] Continuation of Ser. No. 470,876, May 17, 1974, Pat. No. 3,882,028.

[52] U.S. Cl. ............................. 250/361 C; 23/254 E
[51] Int. Cl.² ............................................ G01T 1/20
[58] Field of Search ............... 250/361 C; 23/232 E, 23/254 E; 328/151; 324/58.5 A

[56] References Cited
UNITED STATES PATENTS

| | | | |
|---|---|---|---|
| 3,447,089 | 5/1969 | Foley | 328/151 |
| 3,528,779 | 9/1970 | Fontijn | 250/361 C |
| 3,710,107 | 1/1973 | Warren et al. | 250/361 C |
| 3,723,736 | 3/1973 | Laney | 250/361 |
| 3,734,691 | 5/1973 | Kukla et al. | 23/254 E X |
| 3,746,513 | 7/1973 | Warnick et al. | 250/361 C |
| 3,776,380 | 12/1973 | Damm et al. | 324/58.5 A |
| 3,882,028 | 5/1975 | Zolner | 250/361 C |

*Primary Examiner*—Davis L. Willis
*Attorney, Agent, or Firm*—James L. Neal

[57] ABSTRACT

Apparatus disclosed herein provide simple means for observing chemiluminescent reactions and for measuring the concentrations of several constituents of a gaseous sample substantially simultaneously, as for example the concentrations of $NO_x$, NO and $NO_2$ in a mixture of other gases. Chemiluminescence is induced by the spontaneous reaction of selected constituents with reagents in a plurality of small reaction chambers confronting a single sensitive photodetector. The reation chambers utilize concentric feed nozzles to enhance the intimate mixing of reactants to promote more complete and rapid reaction near ambient pressure in a minimized space.

20 Claims, 1 Drawing Figure

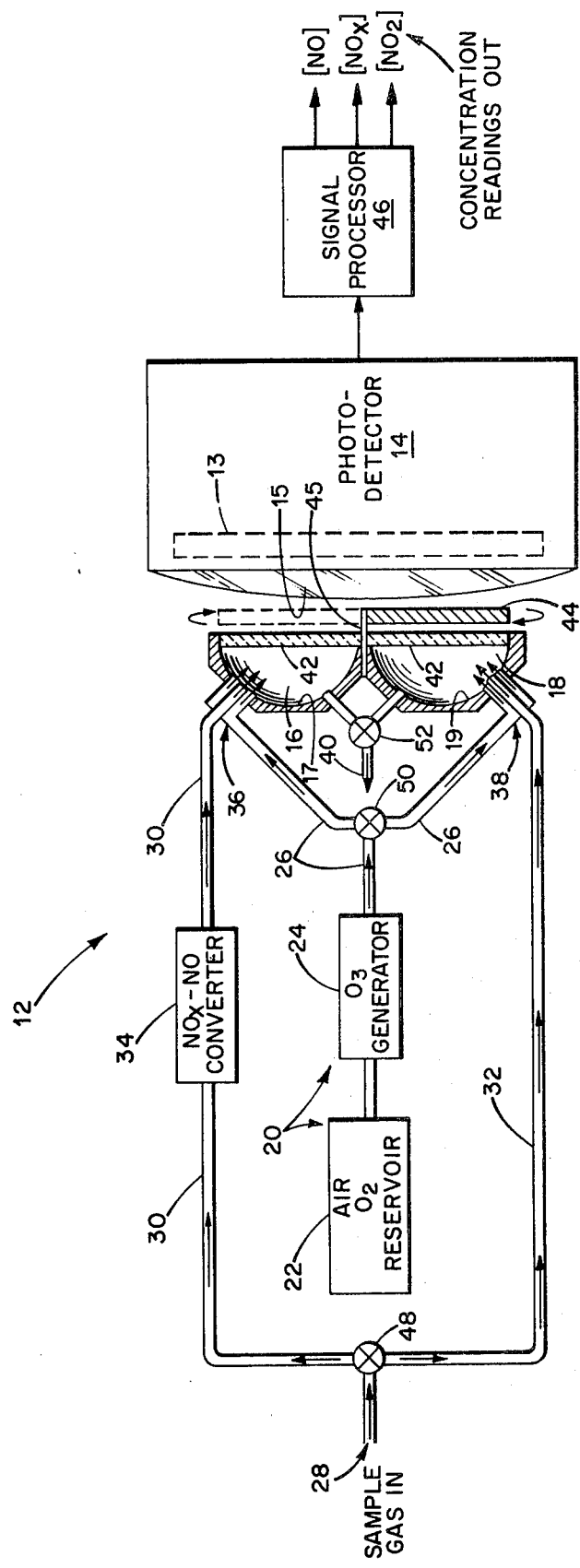

MULTIPLE CHAMBER CHEMILUMINESCENT ANALYZER

CROSS REFERENCE TO RELATED APPLICATION

This application is a continuation of an application Ser. No. 470,876 filed May 17, 1974 for "Multiple Chamber Chemiluminescent Analyzer" by William J. Zolner, now issued U.S. Pat. No. 3,882,028.

BACKGROUND OF THE INVENTION

This invention relates to apparatus for observing chemiluminescent reactions and more particularly to apparatus employing a single photodetector and a plurality of chambers wherein chemiluminescent reactions may occur.

Because of efforts being undertaken to reduce atmospheric pollution, reliable methods are needed for monitoring the level of various individual noxious gases in both the ambient atmosphere and various effluent sources, such as vehicle exhaust and the like. The detection of the presence of pollutants in sub-part-per-million levels by the observation of chemiluminescent reaction is particularly attractive because the method can be adapted to be continuous and because long path length observation is not required, as in absorption spectroscopy. A chemiluminescent reaction occurs where a primary reactant such as nitric oxide (NO) or carbon monoxide (CO), which are common pollutants, engage in a highly exothermic reaction with certain second reactants, or reagents, such as atomic oxygen (O) or ozone ($O_3$) to emit radiant energy usually in the infrared region. The mechanism and kinetics of the chemiluminescent reaction of NO with $O_3$ have been described by P. N. Clough and B. A. Thrush, Trans. Faraday Soc. 63, 915 (1967). Sensitive detectors can be calibrated to respond to the chemiluminescent emission in proportion to the concentration of the primary reactants in the sample. Methods have been devised to measure the concentration of substances which are not directly measureable by chemiluminescent reaction but which bear an ascertainable relation to substances which do. For example, the concentration of $NO_x$, which is the mixture of NO and $NO_2$, as well as the concentration of NO and $NO_2$ are of interest in applications such as the measurement of vehicle emission and the like. However, $NO_2$ does not readily react with ozone or the like in a chemiluminescent reaction. $NO_2$ may be converted to NO by appropriate catalytic or reactive methods, permitting the measurement of $NO_x$ by the chemiluminescent measurement of the equivalent amount of NO. The concentration of $NO_2$ may be determined thereafter by comparing the measured concentration of NO with measured concentration of $NO_x$.

In some applications it is desirable to observe the chemiluminescent reactions of interest under reaction conditions of very low pressure. However, systems have been devised which operate satisfactorily near ambient pressure, thus eliminating the requirement of a cumbersome and expensive vacuum system for maintaining low pressures. It remains necessary to employ a reaction volume at least large enough to observe and detect measurable chemiluminescence, the extent of which is measurably decreased as pressure is increased. This decrease in measurable chemiluminescence is commonly denoted as the quenching effect.

Other limitations include the effects of short-term ambient noise on the sensitivity of the detection system. Noise effects can be reduced by optical chopping techniques known to the art and by signal integration over relatively long sampling periods (greater than a few seconds).

Some of the sampling and integration techniques known to the art include the comparison of data obtained during substantially different time intervals. If, however, the concentrations of the substances to be measured vary substantially from one period to the next, the data obtained may be meaningless. One technique which overcomes this disadvantage is the simultaneous measurement of several samples, which permits the simultaneous comparison of data. According to the aforementioned detection technique, more than one detector is employed, typically one detector per reaction chamber. Since detectors tend to be bulky and expensive and since detectors having substantially identical operating characteristics are difficult to provide, thereby admitting to a margin of error in response among nonidentical detectors, it is advantageous to employ a single detector to perform all measurements.

It is, therefore, an object of the present invention to provide apparatus for observing chemiluminescence in a sample.

It is a further object to provide apparatus for analyzing a variety of samples substantially simultaneously.

It is a further object to provide apparatus for chemiluminescent analysis having a minimum number of detectors.

It is a further object to provide apparatus having reaction chambers wherein observable chemiluminescent reaction may occur near ambient pressure.

It is further an object of this invention to minimize the volume of reaction chambers wherein observable ambient pressure chemiluminescent reactions may occur in order to maximize the number of reaction chambers which may be viewed by a single photodetector.

It is further an object of this invention to minimize the size and expense of a detection system comprising reaction chambers and a photodetector.

It is further an object of the invention to provide apparatus for continuous and substantially simultaneous analysis of at least two constituents in a sample.

It is a further object of this invention to minimize the effects of ambient noise and component instability in a chemiluminescent analyzer.

Other objects and features will be in part apparent and in part pointed out hereinafter.

SUMMARY OF THE INVENTION

According to a preferred embodiment of the present invention, apparatus is adapted for measuring concentrations of constituents in a gas near ambient pressure by measuring the extent of chemiluminescent reaction which may occur in each of several small reaction chambers. In order to counteract the quenching effect associated with chemiluminescent reactions, which occur above relatively low pressures, and in order to promote more complete and rapid reactions in a reduced volume, each reaction chamber utilizes a concentric feed nozzle, wherein an orifice for a first reactant, such as the sample, is circumscribed by an opening for a second reactant, such as ozone, and whereby the reactants are introduced at moderate pressure in intimate mixture into a relatively small volume reaction chamber. The inlet of the nozzle is disposed to be in clear view of a sensitive photodetector such as a photomultiplier tube. The use of the concentric feed technique to supply reactants into a reaction chamber adapted for operation near ambient pressure serves to minimize the size requirements of the individual reaction chambers and thus to maximize the number of reaction chambers which can be viewed simultaneously by a single photo-multiplier tube, or the like, of conventional size.

Chopping of the optical output of the reaction chambers serves a two-fold function. First, the optical output of a single reaction site is periodically coupled to, i.e., blocked from, the detector, where the output is sampled in order to reduce ambient short-term noise in accordance with conventional sampling theory and usage. Second, the output from each individual reaction chamber is coupled to the detector in rapid periodic sequence, thereby producing time-wise interlaced, i.e., time-multiplexed output data from the detector.

Signal processing means cooperate with the chopping means to discriminate between the various sources of data, i.e. to demultiplex, to collect the data, to temporarily store the data for the purposes of signal processing, and to derive therefrom information indicative of the relative concentration of constituents in the sample, such as NO and $NO_x$. The signal processing means includes means for the determination of the relative concentration of constituents not directly observable by chemiluminescence or not distinguishable by observation of less than two samples, as for example $NO_2$. The relative concentration of $NO_2$ may be derived from the comparison of the relative concentrations of NO and $NO_x$, which have been determined by substantially simultaneous observation of separate subsamples of the same sample. Signal information may also be processed to provide substantially simultaneous output of data indicating the concentration of more than one constituent or group of constituents.

Optical filter means are employed in order to improve the selectivity of the detection apparatus. Filter means may, in addition, serve as optical windows for the reaction chambers.

Besides other advantages herein stated or herein apparent, the above embodiment of the present invention eliminates the substantial expense and bulk of a multiplicity of detectors as well as the practical problems of matching different detectors so as to minimize the effects of differences in characteristics.

BRIEF DESCRIPTION OF THE DRAWING

The single FIGURE is a diagram, partially in schematic form, of a gas analyzer constructed in accordance with a preferred embodiment of the present invention.

DETAILED DESCRIPTION OF THE PREFERRED EMBODIMENT

The embodiment described hereinafter by way of illustration is an apparatus for pollution studies for measuring the concentrations of NO, $NO_x$ and $NO_2$ in a sample of gas. The physical arrangement of the system and wavelength regions of observation are correspondingly selected. It should be understood, however, that appropriate changes may be made for detecting and analyzing other substances, e.g., ammonium ($NH_3$), oxides of carbon ($CO_x$), oxides of sulfur ($SO_x$), hydrocarbons (HC), ozone ($O_3$), and for utilization of the invention for different purposes, such as observing chemiluminescence in substances such as organic dyes. Similarly, the embodiment of detection means and signal processing means described herein are by way of illustration and are not intended to limit the scope of the invention.

Referring to the single FIGURE, a gas analyzer is shown, wherein a sensitive photodetector 14, such as a photo-multiplier tube having a photocathode 13, has a window 15 confronting a first reaction chamber 16 and a second reaction chamber 18. A reagent supply system 20 is shown, which includes an air or oxygen ($O_2$) reservoir 22, an ozone ($O_3$) generator 24 and reagent conduits 26 for carrying the reagent $O_3$ to the reaction chambers 16 and 18. A sample inlet 28 is for receiving samples containing constituents to be measured, such as NO or $NO_x$. The samples are transmitted by a first chamber sample conduit 30 and a second chamber sample conduit 32. A $NO_x$ to NO converter 34 is for processing samples supplied to the first chamber 16 to produce, from $NO_x$, NO in proportion to the concentration of $NO_x$. A first concentric nozzle 36 is for supplying samples and reagents in intimate mixture to the first chamber 16, and a second concentric nozzle 38 is for supplying the second reaction chamber 18 in a similar manner. In this embodiment the concentric nozzles 36, 38 are disposed to face the photodetector 14. Products of reaction are drawn from the chambers 16, 18 through an exhaust 40. Optical filter means 42, covering the chambers 16 and 18 are for selectively attenuating radiant energy emitted by chemiluminescent reaction in the chambers 16 and 18 in spectral regions not of interest for the purposes of analysis. Optical coupling means, or that is to say, chopping means, 44 between the chambers, 16 and 18, and the photodetector 14 are for alternately blocking and unblocking in rapid succession emitted radiation directed for the chambers, 16 and 18, toward the photodetector 14. Chopping action produces at the photodetector 14 time-multiplexed data about the concentration of constituents in each chamber, 16 and 18. A signal processor 46 is for demultiplexing and interpreting the data from the photodetector 14. Valves 48, 50 and 52 are provided for convenience of controlling the rates and paths of gas flow.

The signal processing means 46 operates according to principles of information processing and signal detection known to the art, such as time-multiplexing, analog envelope detection, or digital photon-counting detection. Accordingly, the signal processor 46 demultiplexes the data from the detector, collects it and stores it temporarily in separate storage means, such as a capacitor or a memory register, depending upon the mode of detection or the mode of storage adopted, and prepares it for further processing or for output. For example, according to the operation of the present embodiment, chemiluminescent reaction in the first chamber 16 yields information indicative of the concentration of $NO_x$ in the sample and chemiluminescent reaction in the second chamber 18 yields similar information about NO. Since $NO_x$ is the mixture of NO and $NO_2$, the concentration of $NO_2$ is easily computed by subtracting measured values for the concentration of NO from those values for $NO_x$. When the concentration of the substances analyzed do not fluctuate substantially in comparison to the rates of measurement and computation, the above method of analysis should yield reliable results.

The concentric feed nozzle, as at 36 and 38, has been demonstrated to be very effective in mixing reactants near ambient pressure upon entrance into a relatively small reaction chamber. Compared with chambers of identical size having two-nozzle inlets for mixing, twice as much chemiluminescence has been observed. As a result of the apparent increase in chemiluminescent efficiency, chambers of considerably smaller volume may be utilized for observing such reactions without apparent loss in overall sensitivity. Therefore, several chambers may be arranged confronting the window of a conventional photo-multiplier tube. The FIGURE illustrates an embodiment having two reaction chambers. However, up to five chambers of essentially the same size may be arranged as shown confronting the window 15 of the photo-multiplier tube which is typically about two inches in diameter.

The chopping means 44 shown in the FIGURE is a mechanical device located conveniently between the photodetector 14 and the chambers 16 and 18. Chambers 16 and 18 attach to the window 15 of the photo-multiplier. It may be a thin rotating disc having a slit or other convenient opening, or it may be a reciprocating device. A rotating chopping means offers the advantage of low vibration operation and simplicity. Except for the intercession of this mechanical device, the reaction chambers 16 and 18 would preferably impinge upon the window 15 of the photo-multiplier tube for minimizing the optical path lengths. Although more than one chamber may be viewed simultaneously by the photodetector, according to the present application the chopping means 44 allows that typically no more than one chamber is visible at any instant. The chopping means 44 cooperates with the signal processor 46 by means of timing, positioning, or other means of synchronization to discriminate between the signals derived from the reactions in selected individual chambers.

Other means of chopping known to the art may also be employed such as electrostatic or electromagnetic focussing means cooperating with the photocathode 13 of a photo-multiplier-type photodetector 14, movable reflectors and refractors, such as prisms, or the like. Due consideration must be made for the inherent expense of such systems and for decreased sensitivity resulting from reflections, increases in radiant energy path length, size limitations and the like. A chopping means which minimizes optical path length and thereby minimizes optical losses is preferred. A possibly suitable electrostatic photo-multiplier system employing electrostatic chopping is manufactured by SSR Instruments, 1001 Colorado Boulevard, Santa Monica, California.

Optical filter means 42 are shown covering the reaction chambers 16 and 18. A single filter may cover all reaction chambers, or each chamber may have individual filter means comprising one or more optical elements. A filter may function as a wall of the reaction chambers, i.e. as an optical window, in addition to its function of attenuating radiant energy transmission outside of spectral regions of interest. For an apparatus for analyzing NO, a cut-off filter which absorbs substantially all emissions below 600 nm while transmitting substantially all emission in the infrared region substantially reduces unwanted emissive noise. An example of a suitable filter available commercially is the Corning CS 2-60 filter manufactured by Corning Glass Works, Corning, New York.

Since it is often desirable to measure emissions from substances of extremely low concentration, for example less than 10 parts per billion, highly sensitive photodetectors are required. Photodetectors known to the art suitable for herein-described infra-red detection applications include refrigerated photomultiplier tubes, such as the ERMA-II, RCA Model 8852, available from RCA Electronic Components, New Holland Avenue, Lancaster, Pennsylvania.

Additional techniques by which apparent sensitivity can be enhanced include utilizing reflective coatings, such as gold, on inside walls 17 and 19 of the reaction chambers 16 and 18 opposite the photodetector window 15 and employing reaction chambers of appropriate shape and nozzles of appropriate orientation for directing substantially all emission toward selective sensitive portions of the photocathode 13. For instance, a reaction chamber of concave shape as shown in the FIGURE having gold reflective coatings on the inner walls 17 and 19 opposite the optical window 15 tends to direct the radiant emission through the window 15 to the center of the surface of the photocathode 13. The area near the geometric center of the photocathode 13 is often intended to be most sensitive to incident radiant energy. It is of course possible for other regions of maximum sensitivity to exist on the surface of the photocathode. The arrangement and orientation of the reaction chambers may therefore be appropriately modified.

In the illustrative embodiment, a converter 34 is employed to chemically process some constituents in the sample to form products susceptible to chemiluminescent reaction. By appropriate calibration, the resultant chemiluminescent reaction yields information indicative of the concentration of constituents not directly observable. The preferred embodiment may employ a $NO_x$-to-NO reactive or catalytic converter of which many are known to the art. Suitable $NO_x$-to-NO converters are manufactured by the assignee of the present application, by Beckman Instruments, Fullerton, California, and by Monitor Labs, Inc., 4202 Sorrento Valley Boulevard, San Diego, California.

The illustrative reagent supply system 20 includes a reservoir 22 for containing air or oxygen and an ozone ($O_3$) generator 24. The ozone generator 24 converts oxygen to ozone by means well known to the art, such as electrical discharge or ultraviolet irradiation. Where the ambient air supply is a suitable source of oxygen, a reservoir may be unnecessary.

By way of summary, the operation of the illustrative embodiment is as follows. Sample gas enters the sample inlet 28 and is divided and directed at the inlet valve 48. One portion of the sample is processed by the converter 34 and is subsequently supplied to the first small reaction chamber 16. A second portion of the sample is supplied directly to the second small reaction chamber 18. The reagent supply system 20 supplies an appropriate amount of a suitable reagent, in this case ozone, to each of the small reaction chambers 16 and 18. Concentric nozzles 36 and 38 facing the photodetector 14 promote the mixing, and thereby the reaction, between samples and reagents introduced near ambient pressure into the small reaction chambers 16 and 18. The reactions emit radiant energy, which is selectively attenuated by the optical filter means 42. A chopper 44 alternately blocks the passage of emissions from each of the small chambers 16 and 18 which are directed toward the window 15 of the photo-multiplier tube 14, so that the photo-multiplier tube 14 receives a sequence of signals alternately from each of the small reaction chambers 16 and 18. The signal processor 46 separates the signals and produces an output indicative of the concentration of one or more of the concentrations in the sample, in this case NO, $NO_x$ and $NO_2$.

In view of the foregoing, it may be seen that several objects of the present invention are achieved and other advantageous results have been attained.

As various changes could be made in the above construction without departing from the scope of the invention, it should be understood that all matter contained in the above description or shown in the accompanying drawing shall be interpreted as illustrative and not in a limiting sense.

I claim:

1. Apparatus for observing chemiluminescent reaction comprising:
   a plurality of reaction chambers having optical openings therein;
   means for supplying reagents and samples to each of said reaction chambers;
   a photodetector spatially arranged to observe sites of reaction in each of said chambers for detecting radiant energy given off as a result of chemiluminescent reaction in said chambers and for generating an output responsive to said detected energy; and
   means periodically coupling and uncoupling radiant energy from each of said chambers to said photodetector for forming in said output a sequence of discrete time-wise interlaced signals.

2. Apparatus according to claim 1, wherein said photodetector is a photomultiplier providing an output which is essentially proportional to the detected radiant energy.

3. Apparatus according to claim 2, wherein said radiant energy coupling means comprise means periodically blocking and unblocking in alternating sequence the optical paths between each of said reaction chambers and said photomultiplier.

4. Apparatus according to claim 3, further comprising optical spectrum selection means for attenuating a selected spectrum of the radiant energy prior to detection by said photomultiplier.

5. Apparatus according to claim 1 further comprising means for comparing said discrete time-wise interlaced signals for generating a sequence of signals derived therefrom.

6. Apparatus for observing chemiluminescent reaction comprising:
   a plurality of reaction chambers having optical openings and adapted for containing gases near ambient pressure therein;
   means for supplying reagents and samples to each of said reaction chambers, whereby reagents and samples intimately mix upon entrance into said chambers to interact in substantially complete chemical reaction;
   a photodetector having a window and optical detection means therein, said wndow confronting substantially all reaction sites in said chambers, said chambers being fixed in relation to said window of said photodetector for detecting radiant energy emitted as a result of chemiluminescent reaction in said chambers and for generating an output essentially proportional to the detected radiant energy; and
   means periodically coupling and uncoupling emitted radiant energy from each of said reaction chambers to said photodetector for forming in said output a sequence of discrete timewise interlaced signals, each signal containing information indicative of the quantity of radiant energy emitted from one of said chambers during one coupling event.

7. Apparatus according to claim 6, wherein said photodetector comprises a photomultiplier and said optical detection means comprise a photocathode, and wherein said radiant energy coupling means comprise means for directing emitted radiant energy from each of said reaction chambers to selected spatial portions of said photocathode.

8. Apparatus according to claim 7 wherein said radiant energy coupling means further comprise electrostatic deflection means, and wherein said reaction chambers impinge upon said photodetector window minimizing optical path lengths from said detector to said sites of reaction.

9. Apparatus according to claim 7, wherein said radiant energy coupling means further comprise electromagnetic deflection means and wherein said reaction chambers impinge upon said photodetector window for minimizing optical path length from said detector to said sites of reaction.

10. Apparatus according to claim 6, wherein said radiant energy coupling means comprise means sequentially blocking and unblocking the optical paths between each of said reaction chambers and said photodetector.

11. Apparatus according to claim 10 further comprising means mounting said reaction chambers closely adjacent said photodetector for minimizing said optical paths.

12. Apparatus according to claim 11, wherein said optical blocking means comprise a rotating element having at least one space therein for the passage therethrough of radiant energy emitted from said chambers and directed toward said photodetector.

13. Apparatus for chemiluminescent analysis comprising:
   a plurality of reaction chambers spatially arranged in close proximity adapted for containing gases at near ambient pressure and having openings therein spatially arranged for viewing substantially all reaction sites therein from a point on one surface on a plane external to all of said chambers;
   means for supplying reagents and samples to each of said chambers, whereby reagents and samples intimately mix upon entrance into said chambers for engaging in chemiluminescent reaction emitting radiant energy in proportion to the extent of said reaction in said chambers;
   a photodetector having a window and optical detection means therein, wherein said window is closely adjacent and in view of substantially all reaction sites in said chambers, said chambers being fixed in relation to said photodetector, for detecting radiant energy emitted as a result of chemiluminescent reaction in said chambers and for generating an output essentially proportional to the detected radiant energy;
   optical spectrum selection means for transmitting only a portion of a selected spectrum of said emitted radiant energy to said photodetector;
   means successively coupling and uncoupling radiant energy emitted from each of said chambers to said optical detection means in said photodetector for forming in said output a rapidly occurring sequence of discrete time-wise interlaced signals, each signal containing information indicative of quantity of radiant energy emitted from one of said chambers; and signal processing means for discriminating between said signals and for interpreting said signal information.

14. Apparatus according to claim 13 wherein each said reaction chamber comprises a concave cavity having an inner surface reflective to radiant energy emission disposed to direct said emission toward said photodetector and wherein said means for supplying reagents and samples directs such samples and reagents towards said photodetector.

15. Apparatus according to claim 14 wherein said photodetector comprises a photomultiplier and said radiant energy coupling means comprise means sequentially blocking and unblocking the optical paths between each of said reaction chambers and said photomultiplier.

16. Apparatus according to claim 15 wherein said optical blocking means comprise a rotating element having at least one space therein for the passage of radiant energy emitted from said chambers and directed toward said photomultiplier.

17. Apparatus adapted for measuring constituent concentration by chemiluminescent analysis comprising:

a plurality of reaction chambers adapted for containing gases at near ambient pressure spatially arranged in close proximity and having optical openings therein spatially arranged for viewing substantially all reactions therein through an aperture in a plane external to all of said chambers;

means arranged to introduce reagents and samples in intimate proximity into each of said reaction chambers toward said aperture, whereby reagents and samples contain substances disposed to chemiluminescent reaction with one another interact in rapid and substantially complete chemiluminescent reaction emitting radiant energy in substantial proportion to the concentration of known constituents in the samples;

a photodetector comprising a photomultiplier having a window of less than two inches width spatially arranged closely adjacent the optical openings of all of said reaction chambers and fixed with respect thereto for detecting radiant energy given off by chemiluminescent reaction in said chambers and for generating an output essentially proportional to the detected radiant energy;

optical filter means located between said photodetector and sites of chemiluminescent reaction in said chambers for attenuating radiant energy transmission outside the spectrum of interest;

mechanical means for sequentially chopping the optical paths between each of said optical openings and said window for periodically coupling and uncoupling radiant energy emitted from each of said reaction chambers with said photodetector and for forming in said output a rapidly occurring sequence of time-wise interlaced signals each signal containing information indicative of the concentration of at least one constituent in each of said chambers; and signal processing means for discriminating between said signals and for interpreting and comparing said signal information to indicate the concentration of selected constituents in the samples.

18. Apparatus according to claim 17 wherein said optical blocking means comprise a thin rotating disk element having at least one space therein for the passage of emitted radiant energy from said chambers to said photodetector.

19. Apparatus according to claim 17 wherein said signal processing means are adapted to analyze the concentration of the oxides of nitrogen in reaction with ozone.

20. Apparatus according to claim 17 wherein the average diameter of each of said reaction chambers is less than one-half the width dimension of said photodetector window.

* * * * *